United States Patent
Hanisch et al.

(10) Patent No.: US 10,806,908 B2
(45) Date of Patent: Oct. 20, 2020

(54) BALLOON CATHETER

(71) Applicant: InnoRa GmbH, Berlin (DE)

(72) Inventors: Uli Hanisch, Berlin (DE); Ulrich Speck, Berlin (DE)

(73) Assignee: INNORA GMBH, Berlin (DE)

( * ) Notice: Subject to any disclaimer, the term of this patent is extended or adjusted under 35 U.S.C. 154(b) by 333 days.

(21) Appl. No.: 14/785,877

(22) PCT Filed: Apr. 16, 2014

(86) PCT No.: PCT/EP2014/057701
§ 371 (c)(1),
(2) Date: Oct. 21, 2015

(87) PCT Pub. No.: WO2014/173748
PCT Pub. Date: Oct. 30, 2014

(65) Prior Publication Data
US 2016/0067460 A1 Mar. 10, 2016

(30) Foreign Application Priority Data
Apr. 22, 2013 (DE) .................. 10 2013 104 029

(51) Int. Cl.
*A61M 25/10* (2013.01)
(52) U.S. Cl.
CPC ... *A61M 25/1006* (2013.01); *A61M 2025/105* (2013.01); *A61M 2025/1068* (2013.01)
(58) Field of Classification Search
CPC ........ A61M 25/1006; A61M 2025/105; A61M 2025/1068
See application file for complete search history.

(56) References Cited

U.S. PATENT DOCUMENTS 4,276,874 A * 7/1981 Wolvek ............ A61M 25/0054
600/18
4,813,934 A * 3/1989 Engelson .......... A61M 25/0075
604/99.02
(Continued)

FOREIGN PATENT DOCUMENTS

EP 1372737 A2 1/2004
EP 2170421 A2 4/2010
(Continued)

OTHER PUBLICATIONS

International Preliminary Report on Patentability with Search Report in International Application No. PCT/EP2014/057701, dated Oct. 22, 2015.
(Continued)

*Primary Examiner* — Manuel A Mendez
*Assistant Examiner* — Courtney B Fredrickson
(74) *Attorney, Agent, or Firm* — Millen White Zelano & Branigan, PC; Brion P. Heaney

(57) ABSTRACT

A balloon catheter for treating elongate diseased vessels with a variable diameter, comprising a pre-stretched balloon and a catheter shaft, which forms a wire lumen embodied to guide a guide wire and forms a liquid lumen by which a liquid can be fed to the balloon. The balloon is fastened to a first catheter shaft element at a first, proximal fastening site and fastened to a second catheter shaft element at a second, distal fastening site, wherein the second fastening site is movable along a longitudinal axis of the catheter shaft in relation to the first fastening site. The balloon surrounds a section of the catheter shaft which extends between the first and second fastening sites. Here, the section of the catheter shaft surrounded by the balloon encloses different regions of the catheter shaft with a changing longitudinal extent of the balloon.

16 Claims, 2 Drawing Sheets

(56) References Cited

U.S. PATENT DOCUMENTS

Figure 1:
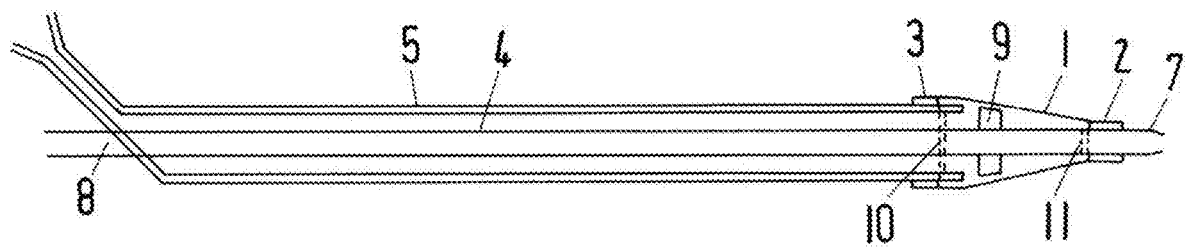

| | | | |
|---|---|---|---|
| 5,103,402 | A | 4/1992 | Morton et al. |
| 5,304,121 | A | 4/1994 | Sahatjian |
| 5,383,856 | A | 1/1995 | Bersin |
| 5,879,499 | A | 3/1999 | Corvi |
| 6,344,045 | B1 * | 2/2002 | Lim .................. A61F 2/958 |
| | | | 604/194 |
| 6,616,650 | B1 | 9/2003 | Rowe |
| 7,179,251 | B2 | 2/2007 | Palasis |
| 7,473,242 | B2 | 1/2009 | Donovan et al. |
| 7,753,926 | B1 | 7/2010 | Pacetti |
| 7,846,147 | B2 | 12/2010 | Wang |
| 8,066,667 | B2 | 11/2011 | Hayman et al. |
| 8,216,267 | B2 | 7/2012 | Pallazza |
| 8,244,344 | B2 | 8/2012 | Wang |
| 8,292,912 | B2 | 10/2012 | Burton et al. |
| 2005/0037048 | A1 * | 2/2005 | Song .................. A61L 27/54 |
| | | | 424/423 |
| 2005/0102019 | A1 * | 5/2005 | Yadin .................. A61F 2/82 |
| | | | 623/1.11 |
| 2005/0197668 | A1 * | 9/2005 | Lim .................. A61M 25/1002 |
| | | | 606/194 |
| 2006/0287665 | A1 | 12/2006 | Burton et al. |
| 2008/0082050 | A1 * | 4/2008 | Solar .................. A61B 17/12022 |
| | | | 604/164.13 |
| 2008/0243103 | A1 | 10/2008 | Whetham et al. |
| 2009/0018501 | A1 | 1/2009 | Yribarren et al. |
| 2009/0030494 | A1 | 1/2009 | Stefanadis et al. |
| 2009/0104246 | A1 | 4/2009 | Falotico |
| 2009/0171278 | A1 | 7/2009 | Hirszowicz et al. |
| 2009/0254063 | A1 * | 10/2009 | Oepen .................. A61M 25/1006 |
| | | | 604/509 |
| 2009/0258049 | A1 | 10/2009 | Klein et al. |
| 2010/0239635 | A1 * | 9/2010 | McClain .................. A61L 27/16 |
| | | | 424/423 |
| 2012/0310210 | A1 * | 12/2012 | Campbell .................. A61L 29/16 |
| | | | 604/509 |
| 2015/0112255 | A1 * | 4/2015 | Jensen .................. A61M 25/0054 |
| | | | 604/103.1 |

FOREIGN PATENT DOCUMENTS

| | | |
|---|---|---|
| EP | 2510972 A1 | 10/2012 |
| WO | WO-95/08965 A1 | 4/1995 |
| WO | WO-96/19256 A1 | 6/1996 |
| WO | WO-2005025648 A2 | 3/2005 |
| WO | WO-2007054364 A2 | 5/2007 |
| WO | WO-2011044455 A1 | 4/2011 |
| WO | WO-2011/130679 A1 | 10/2011 |
| WO | WO-2012158944 A1 | 11/2012 |

OTHER PUBLICATIONS

International Search Report from International Application No. PCT/EP2014/057701 dated Aug. 21, 2014.

Scheller, MD, et al., "Paclitaxel Balloon Coating, a Novel Method for Prevention and Therapy of Restenosis", 2004, 110:810-814.

Scheller MD., et al., "Long-Term Follow-Up After Treatment of Coronary In-Stent Restenosis With a Paclitaxel-Coated Balloon Catheter", vol. 5, No. 3, 2012, JACC Cardiovascular Interventions.

* cited by examiner

BALLOON CATHETER

The present invention relates to catheters with a balloon for medical applications.

For various reasons body cavities and blood vessels may require medical treatment with mechanical or pharmacological means. The invention described here relates to medicinal products and methods which expand the range of hitherto available treatment options, and, above all to wall irregularities, structural changes, inflammations, wall thickening and metabolic diseases localised in the wall.

In the case of many diseases of the vascular system and other body cavities, minimally-invasive treatment with catheters has replaced surgery or improved the effectiveness of pharmacotherapy through the targeted local application of medicinal products. Through local administration high drug concentrations can be attained in diseased tissue without, or with a considerably reduced risk of, adverse systemic effects. The focus of development in recent decades has been on the restoration of normal arterial blood flow and the supply of oxygen to downstream tissue in the case of severe arterial narrowing or arterial occlusion. Mostly affected are the coronary vessels, leg vessels, carotids, renal arteries or artificially applied passages such as dialysis shunts. The vessel segments are frequently fibrotically hardened or calcified or blocked by thrombi. To reopen them numerous instruments and aids are available which work in very different ways. Most commonly used are balloon catheters which have a balloon essentially made of non-elastic materials such as nylons. The balloons have a predetermined diameter and a predetermined length, which due to the low elasticity of the material do not essentially change even under high internal pressure. High pressures are required to dilate severely narrowed vascular lumens and make them patent again. The dimensional stability of the balloon prevents the vessel being over-dilated, at least in places where the resistance is lower than in other sections of the diseased vessel.

In order to prevent immediate restenosis occurring through the elastic restoring force of the vessels stents can be implanted.

The pressure exerted on the vessels, and the balloons, which when highly pressurized are hard and stiff, can result in vascular ruptures and detachment of parts of the inner vascular wall (dissections) which acutely impair the blood flow and in a delayed manner can cause the formation of thrombi. In order to reapply dissections to the vascular wall the balloons are inflated for a longer period of up to several minutes or stents are also implanted. Elastic resetting of a vascular wall and dissections are evident immediately after the procedure.

Other methods of dilating or reopening vascular lumens are atherectomy and lasers which can be used over longer sections but cause severe injuries to the vascular wall.

During the course of healing excessive tissue/scar formation can occur which narrows the vascular lumen. This process normally takes months. In most cases it can be prevented by the local administration of medicinal products by means of implanted stents or through the use of special balloon catheters coated with medicinal products.

Drawbacks of the described local treatments of narrowed and occluded arteries are the strict limitation of the treatment to the affected sections of the vessels, i.e. vessels with a diameter constricted to ≤50% of the original diameter. Adjacent diseased sections of the vessels without severe constriction remain untreated so as not to initiate reactive hyperproliferation through mechanical damage. Such adjacent untreated vessel sections are often irregularly formed, inflamed and have deposits (vulnerable plaques) which could break open, release thrombogenic surfaces and lead to sudden vasoconstriction. For the treatment thereof various, also locally very restricted, measures have been proposed, without the benefit of these measures so far being confirmed by clinical studies. Such measures include treating the diseases sections of the vessels by means of stents (e.g. US 2009/104246 A1, US 2009/0030494 A1 with medicinal products), polymers or polymerization (U.S. Pat. No. 7,473, 242, WO 2011/044455, U.S. Pat. No. 7,846,147) or through controlled destruction of the plaque (U.S. Pat. No. 7,753, 926).

There is a lack of a simple, effective treatment method for these elongate diseased vessel segments as part of an angioplasty and/or stent implantation that prevents these vessel sections being by mechanically caused injury damaged in the longer term. There is also no simple treatment of vascular changes at branches.

Balloon catheters coated with medicinal products are described in documents U.S. Pat. Nos. 6,616,650, 5,304,121 and 5,103,402. In animal experiments it could be shown that in spite of the very short contact time between the balloon and the arterial wall, suitable coatings can prevent hyperproliferation after vessel dilation that constricts the lumen (Scheller B., Speck U., Abramjuk C., Bernhard U., Böhm M., Nickenig G. Paclitaxel balloon coating—a novel method for prevention and therapy of stenosis. Circulation 2004; 110:810-814). Clinically, a durable reduction in vascular constriction after angioplasty of very different vessels was seen (e.g. Scheller B., Clever Y. P., Kelsch B., Hehrlein C., Bocksch W, Rutsch W., Haghi D., Diet U., Speck U., Böhm M., Cremers B., Long-term follow-up after treatment of coronary in-stent restenosis with a paclitaxel-coated balloon catheter. J Am Coll Cardiol Intv 2013; 5; 323-330). The coatings used in the cited publications are described in EP 1 372 737 among others. Other patent specifications, such as EP 2170421 and U.S. Pat. No. 8,244,344 describe further possible formulations and methods.

For the above reason, the balloons commonly used in angioplasty are essentially made of non-elastic materials such as nylon. In order to achieve a smaller cross-section for insertion into the artery and to pass these constrictions in the vessel, the balloons are completely emptied, folded and the folds are wrapped around a shaft extending longitudinally through the balloon. These balloons are then filled with liquid at high pressure. They force the lumen to adopt their shape, i.e. the lumen should assume the diameter of the balloon in the area being treated. In doing so serious vascular wall injury usually takes place.

Catheters with balloons of elastic membranes, which can be expanded to a greater of lesser extent with low internal pressures were mainly used for fixing bladder catheters and catheters used for other drainage. Approximately round-shaped balloons are used for this. Accordingly the balloon can and should expand in all directions and not press on certain vascular walls in order to dilate them.

Balloons of easily stretchable materials (e.g. polyurethane, latex, polyisoprene) have also been mentioned in connection with the treatment of irregularly shaped blood vessels (e.g. US 2009/0258049 A1). In other cases soft balloons were preferred for certain applications, e.g. to close openings to aneurysms (U.S. Pat. No. 8,066,667) for the treatment bifurcations (U.S. Pat. No. 8,216,267), for the local administration of medicinal products to the wall of irregularly shaped body cavities (US 2008/0243103 A1) or also for the treatment of irregular and sensitive vascular structures with medicinal products released by the balloons (U.S. Pat. No. 7,179,251, WO 2012/158944). In each case relatively short balloons are involved, up to 4 cm in length where indicated.

A serious problem is the longitudinal expansion of the soft balloon material, as well as in the case of longer balloons the irregular, often only partial or sectional filling. At low pressure the diameter of the balloon increases and at least partially comes into contact with the vascular wall. At the same time the balloon increases in length. As the balloon is proximally and distally fastened to a central shaft, the longitudinal expansion leads to spiral or other type of undesirable deformation of the balloon. To counteract this, the expandable tube can be mounted on the shaft in a pretensioned manner (U.S. Pat. Nos. 6,344,045, 8,066,667). On filling the lumen with liquid the tube initially expands in the desired direction, i.e. it increases in diameter without essential changes in its pre-tensioned length. However, pre-tensioning is only possible if the catheter shaft is rigid. This is undesirable as the catheter has to be guided through the strongly winding vessels.

Another possibility of preventing undesirable longitudinal expansion was proposed in WO 2005/025648: low-elastic threads or textile woven fabrics are embedded in a multiple layer elastic balloon membrane thereby preventing or restricting longitudinal expansion. Drawbacks are the complex construction of the membrane and the associated undesirable increase in thickness.

At high internal pressure a certain increase in length is observed even in the case of balloons with essentially non-elastic membranes. This leads to unwanted curvature of balloons fixed distally and proximally to a non-elastic shaft. By incorporating an element which is elastic in the longitudinal direction in the shaft between the proximally and distally fixed balloon ends, curvature of the balloon can be avoided through small longitudinal extension as the shaft also extends (U.S. Pat. No. 8,292,912).

The aim of the present invention consists in providing a simple and cost-effective catheter with which elongated abnormalities in vessels with different lumen diameters and branches can be treated though mechanical smoothing and local medicinal product administration. It is more particularly the aim of the invention to prevent or restrict deformation of longer expandable catheter balloons during inflation as a result of longitudinal expansion.

This aim is achieved by a balloon catheter according to the invention.

DESCRIPTION OF THE INVENTION

In this description a section lying close to a physician is designated as the proximal section, whereas the section of a catheter to be introduced into a body is designated as the distal section. The term "balloon" is used synonymously as an abbreviation of catheter balloon.

Designated as expandable are balloon membranes which at a difference between the external pressure (pressure in the area surrounding the balloon) and the internal pressure in the balloon of less than 2.0266 bar (2 atm.), i.e. at an internal pressure that is between 0.10133 bar (0.1 atm.) and least than 2.2066 bar (2 atm.) higher than the external pressure, allows the diameter of the balloon to increase at least 2.5-fold perpendicularly to the longitudinal axis, more particularly in a middle section of the balloon, i.e. not at the region of the balloon shoulders at the distal and proximal balloon end, through expansion of the membrane. This applies, for example, if a balloon cross-section of 2 mm in the unfolded, non-tensioned state (internal pressure in the balloon=external pressure) is expanded to 5 mm or more at an internal pressure of <2.0266 bar (2 atm.) above the external pressure. Highly expandable are membranes which under the same conditions allow the balloon diameter to expand at least 5-fold, i.e. in this example to 10 mm. During this, the surface of the balloon increases approximately by the same amount through expansion, i.e. an increase in diameter by 2.5 times corresponds to a surface increase of 2.5 times etc. Designated as elastic or highly-elastic expandable or high-expandable are membranes which on pressure reduction return to approximately the same surface area as before expansion. "Approximately the same" means that the surface of the balloon after expansion is only maximally 25% greater than before expansion. Here, and in the following text, the diameter of the balloon (=balloon diameter) is always taken to mean the diameter perpendicular to the longitudinal axis of the balloon.

In one embodiment the present invention describes a balloon catheter with a balloon and a catheter shaft which forms a wire lumen designed for guiding a guide wire and also forms a liquid lumen via which a liquid can be supplied to the balloon. The balloon is fastened to a first catheter shaft element at a first, proximal fastening site. The balloon is also fixed to a second catheter shaft element at a second, distal fastening site, wherein the first fastening site can be moved along a longitudinal axis of the catheter shaft in relation to the second fastening site. The balloon surrounds a section of the catheter shaft which extends between the first and second fastening site. It is envisaged that the section of the catheter shaft surrounded by the balloon comprises different sections of the catheter shaft as the longitudinal dilation of the balloon changes. Thus, in accordance with the invention the length of the balloon can be adjusted without undesirable deformation and without costly adaptation of the catheter shaft elements. More particularly, it can be envisaged that through the longitudinal expansion of the balloon, areas of the catheter shaft, in particular an inner tube and/or a tube providing the wire lumen, can be surrounded by the balloon that were not surrounded by the balloon before the longitudinal expansion. Longitudinal expansion of the balloon can take place through manual or mechanical displacement of one or both fastening sites and/or manual or mechanical displacement or elastic extension of the first and/or second catheter shaft element. Alternatively, or additionally, longitudinal expansion can take place through supplying the balloon with a liquid via the liquid lumen. In doing so, for example, on filling of the balloon the second catheter shaft element can be moved in relation to the first catheter shaft element through the pressure acting in the longitudinal axis. Through the relative movement of the catheter shaft elements in relation to each other the first and/or second fastening site can be carried along and moved relative to each other. In general, linked to a relative movement of the fastening elements with regard to each other is a movement along a longitudinal axis of the catheter shaft and/or a change in length of the balloon tensioned and/or held between them, more particularly an extension in length if the fastening elements and/or the assigned catheter shaft elements move apart from each other. The first catheter shaft element and the second catheter shaft element can be detachably fastenable with regard to each other and/or selectively displaceable with regard to each other, through a detachable clamp connection for example. The first catheter shaft element can, more particularly, be a tube through which the balloon is filled with or emptied of liquid. Thus, the fluid lumen can be provided or formed by the first catheter shaft element. The first catheter shaft element can be an outer tube in which an inner tube is at least partially accommodated, or a tube which provides the liquid lumen and the wire lumen, a double lumen tube for example. It can be envisaged that the wire lumen and the liquid lumen are formed by tube and/or tube elements fastened to each other. The second catheter shaft element can, in particular, be an inner tube which can contain or form the wire lumen. Such a tube can be at least partially accommodated in an outer tube and be moved with regard thereto. Alternatively the second catheter shaft element can comprise or be formed as a guide element movably borne on an inner tube and/or on a wire guide tube which can contain or form a wire lumen. Such a guide element can be designed as a sliding element and/or a ring or tube section or pipe. A sliding element can in general be in sliding and/or frictionally displaceable and/or at least partially sealing contact with an element which bears it. The inner tube or wire guiding tube on which the guide element is borne in a displaceable manner and/or an element firmly connected thereto or formed in one piece therewith can act or be considered as a first catheter shaft element. It can be envisaged that the second catheter shaft element is arranged distally of and/or can be displaced distally to the liquid lumen and/or an opening via which liquid can be supplied to and/or drained from the balloon via the liquid lumen. The balloon can be fastened directly or indirectly to a first catheter shaft element at the first fastening site in that it is fastened to a component which is fixed relative to the first catheter shaft element and/or is immobile or also movable on the longitudinal axis of the first catheter shaft element. The balloon can be fastened directly or indirectly to the second catheter shaft element at the second fastening site in that it is fastened on a components which is fixed relative to the second catheter shaft element and/or is immobile. The first catheter shaft element and/or the second catheter shaft element, more particularly a tube or inner tube containing or forming the wire lumen can be elastically designed. In general the liquid lumen can be used for filling and/or emptying the balloon. For filling the balloon physiologically tolerable liquids, mostly diluted radiographic contrast agents are preferred.

The balloon can comprise a balloon membrane comprising of or more stretchable elastomers, preferably rubber, latex, polyurethane, isoprene-based polymers or copolymers, silicone, particularly preferably latex, polyurethane or, for example, styrene-isoprene block copolymers such as ChronoPrene® and most preferably Chronoprene®. Chronoprene® is the trademark of the company Cardio Tech International Inc., now AdvanSource Biomaterials, Inc. USA, for a mixture/a block copolymer of polystyrene and hydrated poly-isoprene and additives for improving the strength (polypropylene) and suppleness (mineral oil). In general the balloon can comprise an elastic or highly elastic balloon membrane which moulds well to complex structures.

The length of the balloon in the non-expanded state can be ≥10 cm, preferably ≥15 cm and particularly preferably ≥20 cm. In this way long sections of vessels can be treated and/or supported by the balloon. For use in coronary arteries of other small arteries with lengths comparable to those of the coronary arteries the balloons can be shorter. In the non-expanded state they have a length which is more than 5 times, preferably more than 10 times and particularly preferably more than 15 times the reference diameter of the vessel segment to be treated. In this case the reference segment is the diameter measure in an adjacent non-diseased segment proximal of the diseased segment.

In a further development, as a second catheter shaft element the catheter shaft can comprise an inner tube or elastic material proximal of the first fastening site. More particularly, it can be envisaged that the inner tube exhibits essentially constant elastic properties over its total length and/its length proximal to the second fastening site. On the one hand this allows the elastic properties to be utilized over a great length of the inner tube. On the other hand it is not necessary to use a complex inner tube with different elasticities.

It can be envisaged that a second catheter shaft element designed as the internal tube of the catheter shaft proximally emerges via a seal from a first catheter shaft element designed as the outer tube of the catheter shaft and is arranged or designed to be movable relative to the outer tube. This allows manual displacement of the inner tube by a doctor for example.

The second fastening site of the balloon can be moveable along a longitudinal axis of a first catheter shaft element forming the wire lumen. In this example the second fastening site and/or an element of the catheter on which this is provided, such as the corresponding catheter shaft element and/or the displaceable element can be a guide element which can be designed as a sliding element and/or ring or tube section. The first catheter shaft element can comprise a tube or end section of a tube projecting beyond the liquid lumen. Such a tube or end section can form the wire lumen and/or be designed as inner tube accommodated at least partially within the outer tube and/or define the longitudinal axis along which second fastening site can be moved. The second fastening site can be borne and/or be moved on such a tube. It can be envisaged that the second fastening site is arranged at and/or is moved distally of a liquid lumen and/or an opening of a liquid lumen, via which the balloon is filled and/or emptied. In the same way, the first fastening site can be alternatively or additionally moved via a guiding or sliding element on the first catheter shaft element in the longitudinal direction.

In general it should be noted that a balloon can also be formed by a tube. Preferred is a uniformly patent tube which on inflation evenly increases in diameter over its entire length unless its expansion is restricted by, for example, an irregularly shaped arterial wall. One problem of elongated balloons which through a low internal pressure expand many times over or are highly elastic, is the uniformity of expansion. Frequently the desired increase in the balloon diameter only occurs in one part of the entire balloon, either the proximal or the distal balloon segment. During filling the balloon can burst before it has achieved the required diameter over its entire length, or a further segment, separated from the initially inflated segment, increases in diameter without connecting with the initially filled segment over the entire cross-section. Between the filled segments a septum remains. A septum is a section of the balloon which remains narrow even at high pressure. These not, or only very slightly expanded balloon sections prevent uniform treatment of the vascular wall over the entire length of the balloon ("very slightly"=less than 30% of the diameter perpendicular to the longitudinal axis of the adjacent, expanded balloon segments). Septa occur in particular when long balloons are inflated in tubes which restrict expansion perpendicularly to the longitudinal axis. This is also the case in blood vessels.

The formation of septa is disruptive and undesirable. It can be prevented by expanding the elastic tube sections forming the balloon to their total length at least once, without the expansion of the balloon perpendicularly to the longitudinal axis being restricted. This means expansion perpendicularly to the longitudinal axis by a factor of at least 1.1, preferably to at least 3.0, whereby this refers to the diameter of the balloon before expansion (diameter=expansion of the balloon perpendicularly to the longitudinal axis). After reduction of the internal pressure or removal or other forces causing expansion of the balloon, due to the elastic restoring force the balloon approximately or completely assumes its original smaller diameter (before expansion). The procedure is known as pre-stretching. For pre-stretching, the balloon, or the tube forming the balloon, is filled with gas, for example, until it has expanded over its entire length. Pre-stretching can take place once or several times for various lengths of time. As a result of this pre-stretching or pre-stretching carried out in any other way of the elastic membrane, during subsequent use of the balloon for therapeutic or diagnostic purposes, inhomogeneous filling of the balloon no longer, or only very rarely, occurs.

In addition it was surprisingly found that pre-stretched and contracted tube sections of expandable elastomers forming the balloon can be mounted on conventional catheter shafts stretched in the direction of the longitudinal axis without marked deformations of the catheter shafts occurring, even in the case of large balloon lengths. Pre-stretching in the longitudinal direction advantageously means that an elastic tube section, which is of a defined length when it is unstretched/tension, is by stretched to 20% to 120% of this defined length and then mounted on the catheter shaft while maintaining this stretching or under tension. For example, an elastic tube section, which when unstretched and tension-free is 10 cm long, is stretched to 12 to 22 cm in length and then under tension mounted on the catheter shaft. Preferred is expansion along the longitudinal axis by 30-80%, particularly preferred expansion by 40-60%. On inflation these balloons exhibit neither septa nor much more longitudinal expansion and neither does severe distortion of the section of the catheter shaft under pressure occur. In this way it is possible to produce particularly long, and in the deflated state, particularly thin highly-elastic balloon catheters.

Passage through a haemostatic valve can be facilitated by protective sleeves, whereby after the balloon has passed through the valve the protective sleeve either remains on the shaft or is detached therefrom.

In general, the balloons and/or the catheter shaft can have physiologically tolerable lubricants and/or coagulation inhibitors on their outer surface. In this way the catheter can be easily inserted into a transfer element or a guide catheter and moved in a blood vessel. The risk of thrombi accumulation in areas of low blood flow is minimised.

The balloon can be coated with at least one medicinal product. The balloon is thus suitable for applying medicinal products or other substances directly to treated vascular wall sections. The balloon can be coated with one or more medicinal products at a dose of between 100 µg/cm balloon length and 10 mg/cm balloon length, preferably 300-3000 µg/cm balloon length and particularly preferably 600-3000 µg/cm.

Alternatively or additionally the balloon can be coated with at least one antioxidant, preferably with at least one of the following antioxidants: ascorbic acid, ascorbyl palmitate, butylated hydroxytoluene, butylated hydroxyanisol, nordihydroguaiaretic acid (NDGA), propyl gallate, resveratrol.

The above objective is achieved by catheters, the shaft of which has at least two lumens, wherein one of the lumens can be proximally and distally open for a guide wire and functions as a wire lumen, and one of the lumen can act as a liquid access to a distally mounted elastic balloon, i.e. as a liquid lumen. The distal opening of the liquid access can end in the lumen of the elastic balloon.

In conventional balloons made of relatively non-elastic material, the length of the balloon is firmly limited by the length of the tube on which the proximal and distal fastening sites are located.

In accordance with the present invention, precise determination of the longitudinal expansion of the balloon before use can be dispensed with. The use of the balloons, more particularly elastic balloons is not limited to the treatment of a very restricted section of blood vessel. As, unlike the conventional non-elastic balloons used for the treatment of vascular constrictions, the elastic balloons do not mechanically damage the vascular wall, but adapt to its course, there is no reason to strictly limit the treated area in the proximal or distal direction.

Forms of embodiment of catheters will be explained below by way of the attached figures.

Figure 2A:
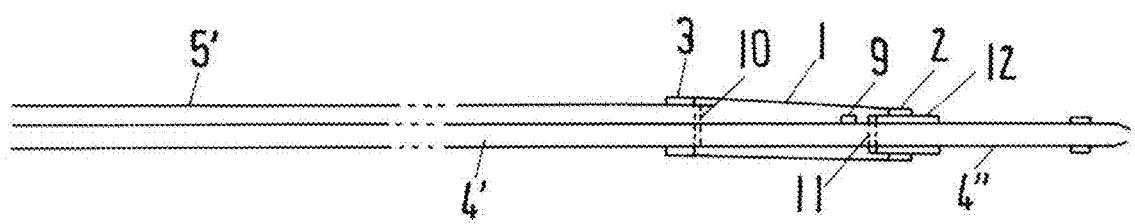
Figure 2B:
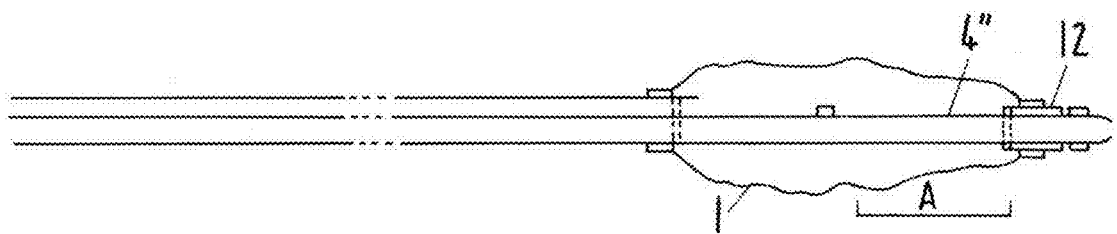
Figure 3B:
Figure 3A:
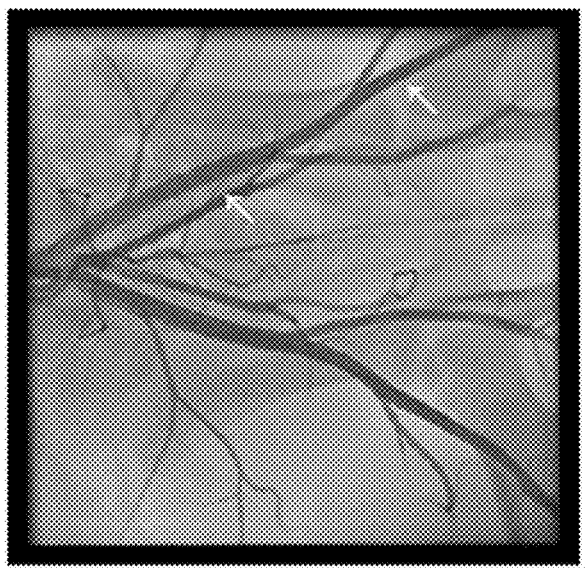

FIG. 1 schematically shows an example of a catheter with an expandable balloon (1) wherein the longitudinal expansion of the balloon is brought about through longitudinal stretching of a tube (4) over the entire length of the shaft;

FIG. 2a schematically shows an example of a further catheter, wherein the longitudinal expansion of the balloon is brought about through a displacement of the distal fastening site (2) on a tube (4') with an end section (4");

FIG. 2b schematically shows the catheter in FIG. 2a after inflation of the balloon in an irregularly formed lumen with expansion of the diameter and the length of the balloon. The letter A denotes the area of the tube (4') with end section (4") which was originally outside the balloon and after longitudinal expansion of the balloon is surrounded by the balloon; and FIGS. 3a and 3b show an example of use of a soft balloon, adaptable in shape, in a narrowing artery segment with side branches.

Whether it is pre-stretched in the direction of the longitudinal axis or not, the longitudinal expansion of the balloon (1) is not hindered. The balloon can expand in the longitudinal direction on and, possibly, together with a central wire-guiding tube, wherein the balloon length is extended with the inclusion of tube lengths or sections which, in the original non-extended state, are outside the balloon lumen or on the other side of the fastening site of the balloon on the tube passing through the balloon. This means that on inflation longitudinal expansion of the balloon is made possible in that the proximal and the distal fastening site at the two balloon ends move away from each other without the extent of the distance essentially being determined by the stretching of the relatively short section of tube located in the balloon. The extent of this possible expansion along the longitudinal axis can at least be the diameter of the balloon in the inflated state, for example ≥5 mm, preferably ≥1 cm, very preferably ≥2 cm and most preferably ≥4 cm. This can be achieved in that the shaft of the catheter comprises two concentric tubes (4, 5) which move with regard to each other (FIG. 1). At the distal end, the balloon (1) is hermetically and firmly attached to the inner tube (4) at a distal fastening site (2), and at the proximal end to the outer tube (5) at a proximal fastening point (3). Thus, in this example, the outer tube (5) acts as a first catheter shaft element on which the first, proximal fastening site (3) of the balloon (1) is envisaged, while the inner tube (4) acts as a second catheter shaft element on which the second distal fastening site (2) is envisaged. The inner tube (4) with the smaller diameter (lumen preferably 0.035"~0.875 mm or 0.018"~0.45 mm or 0.014"~0.35mm) has an end section (4") which can form the distal end (7) of the catheter. It can consist of an elastic material which under slight tension extends distally. Slight tension is defined as a tensile force of 1 kg, the distal extension in the case of a shaft length of 120 cm is at least 0.5-1 cm, preferably ≥2 cm, more preferred ≥3 cm and most preferred ≥4 cm. a the length of the inner tube (4) is considerably greater than that of the balloon, a small perceptual extension of the tube over its length allows considerably elongation of the balloon. To prevent displacement of the inner tube (4) in the proximal direction on shortening of the balloon, e.g. when introducing the catheter through a valve, the inner tube (4) can be provided with stopper or stop (9) which due to its greater diameter prevents retraction of the inner tube (4) into the outer tube (5). Alternatively to expandability in the direction of the longitudinal axis, or additionally, the inner tube (4) can be displaceable with regard to the outer tube (5) over its entire length in the longitudinal direction; in this case a seal allowing the movement can optionally be present with fixers (8). In this way the inner tube (4) can be manually displaced by a doctor and/or through the pressure resulting when filling the balloon is moved in accordance with the longitudinal expansion of the balloon. The balloon can be filled and emptied through the intermediate space between tube (4) and (5) serving as a liquid lumen.

The balloon consists of natural or synthetic polymer elastomers, preferably of rubber, latex, polyurethane, isoprene-based polymers or copolymers, silicone, particularly preferably of latex, polyurethane or ChronoPrene® by CardioTech International, Inc., now AdvanSource Biomaterials, Inc. USA without or with additives or mixtures of different components. Other suitable polymers can be found in the already cited patent specifications (US 2009/0258049 A1, U.S. Pat. Nos. 8,066,667, 8,216,267, US 2008/0243103 A1, U.S. Pat. No. 7,179,251, WO 2012/158944). Other elastomers with the stretchability of the aforementioned products and polymers are also suitable. Substances for improving the mechanical properties, the duration of the shelf life or contrast density are of interest as additives. The contrast density of the balloon membrane can be controlled by the addition of iodinated contrast agent or, for example, through metal powder.

Of particular interest are catheters for the treatment of elongated peripheral arteries with a diameter that reduces considerably over their length. The length of the inflated or expanded balloons can be 2 cm to 40 cm or more, preferably the lengths are between 5 and 35 cm, more preferably between 10 and 30 cm and particularly preferably between 20 and 30 cm. The length of the balloons before inflation or expansion can be ≥10 cm, preferably ≥15 cm and particularly preferably ≥20 cm.

The filling and, in particular, the emptying of such large-volume balloons with contrast agent requires time. Alternatively, filling with absorbent gases, such as carbon dioxide is possible.

The external diameter of a balloon can be between 0.5 and 2.5 mm, preferably between 1 and 2 mm. The balloon material can exhibit these small diameters either, and preferably, in the non-expanded state or it can be folded around the shaft and optionally fixated by means of a retractable thin-walled tube or comparable device.

In the non-expanded state, balloons for small vessels such as coronary arteries have a diameter of 0.5-1.5 mm, in the expanded state up to 6 mm. The preferred lengths are adapted to the lengths of the vessels to be treated, e.g. for coronary vessels at least 10 times the mean diameter of the segment to be treated, for example in the case of a mean vessel diameter of 3 mm the balloon length is ≥30 mm.

The balloon ends are fastened by means of adhesives, or through welding/heat or with solvents through partial solution or by means of threads or with a combination of the various methods, to the fastening sites, such as the shaft or tube, or are connected to a guide element, such as a pipe or ring or tube section which is movable on the tube. At least 2 points the balloon can be directly or indirectly connected via a sliding element to a central tube passing through the balloon in the longitudinal direction, more particularly to a tube and/or inner tube defining a wire lumen. More fastening sites are possible. The fastening to the different fastening sites can take place in different ways.

One possibility of changing the length of the balloon while maintaining the principally cylindrical shape consist in making one of the fastening sites of the balloon displaceable on the longitudinal axis (FIG. 2). Selected as the constant axis is the narrower tube (4') passing though the balloon which acts as the wire guiding tube. Up to around the first proximal fastening site (3), this is guided in a double-lumen tube which has a tube (5') running parallel to the wire guiding lumen (4') forming a liquid lumen. The wire guiding tube (4') has an end section (4") which extends distally beyond the tube (5') forming the liquid lumen. A longitudinal axis is defined by the tube (4') and the end section (4"). On the end section (4"), for example, several centimeters from the distal end a slidable, but closely fitting tube section (12) or a corresponding slidable but closely fitting short pipe is positioned as a guide element. In this example the guide element is thus designed as a sliding element. The distal balloon end (2) is hermetically fastened to the moveable tube section (12). In this example the double-lumen tube/the wire guiding tube (4') and/or the tube (5') fixed relative thereto can be seen as the first catheter shaft element on which the first proximal fastening site (3) for the direct or indirect attachment of the balloon is envisaged. The second, distal fastening site (2) of the balloon is provided on the tube section (12) which is movable relative thereto. On expansion of the balloon the movable tube section (12) can change its position on the fixed tube (4'), more particularly the end section (4") in such a way that the balloon can expand in the longitudinal direction. In the interior of the balloon the tube section (12) can be selected to be so long that its fixes the balloon length to a predetermined minimum value. The movement of the tube section (12) in the proximal direction is, for example, limited by the tube (5') or through other blocks or stops (9) within the balloon lumen. A movement of the tube section (12) formed as the sliding element to distal over the distal end of the end of the tube (4') or the end section (4") can be achieved through an corresponding stop distally or through a fastening on the tube (5') limiting the distal movement. The tube section (12) does not have to form a complete seal with the tube (4') as the pressure in the lumen of the balloon only needs to be slightly greater than the blood pressure and in the case of longer-lasting balloon expansion the pressure and volume can be re-regulated via the syringe filling the balloon lumen. In general the guide element can be designed as a ring and/or tube and/or tube section, more particularly as a short metal pipe and/or a radiopaque tube. Alternatively or additionally the guide element can in general have a radiographic marker (11) particularly the area of the start of the balloon. As in this case the longitudinal movement of the tube does not have to take place via elastic elongation of the tube (4'), the catheter shaft can in general be a uniform double-lumen tube. One of the lumens, particularly the wire lumen formed by the tube (4') extends to distal through the balloon, the other lumen fills and empties the balloon and acts as a liquid lumen.

The measures described above prevent or restrict irregular deformation of a balloon which is fixed at two ends and expands under pressure in the longitudinal direction. This relates in particular to balloons which at a pressure of ≤4 bars and free expansion increase their original (measured without pressure) length by more than 5%. The above-described methods are preferably used for balloons which under these conditions increase in length by ≥10%, more particularly for balloons which increase in length by ≥25%. In accordance with the present invention the length of the balloon is not restricted by internally or externally limiting elements, such as a retractable outer tube.

Otherwise the catheter structure corresponds to that of conventional angioplasty catheters in terms of materials, dimensions, the grip, number of connections for syringes, the catheter shaft, with radiopaque or magnetic markers (10, 11), preferably close to the fixing point of the balloon on the shaft, with the lumen for filling and emptying the balloon and with a lumen for a guide wire, either over the entire shaft length or only the distal section thereof (rapid-exchange version). The shaft can be provided with more than one balloon and with more lumens than a wire and a liquid lumen. The shaft, or sections thereof, and the balloon can be lubricated with special coatings.

The elastic balloon can be coated with one or more lubricants or with one or more medicinal products or with any mixtures of lubricants and medicinal products. Auxiliary agents or additives and be added to the coating. If the coating is applied in liquid form, solvents are suitable which do not, or only to a minor extent attack the balloon material, and distribute evenly on the balloon surface. Preferable are easily volatile solvents such as, for example, methanol, ethanol, propanol or isopropanol, acetone, dimethyl formamide, acetonitrile, ethyl acetate, hexane, heptane or mixtures thereof and water as a further solvent or an additive to organic solvents.

Suitable coating solutions, compositions and methods are described in the patent specifications cited above. The elastic balloons can be coated in the contracted or slightly or fully expanded state. In order to achieve even partial expansion the balloons are expanded in a pipe, possibly provided with a lubricant layer, the internal pressure of the balloon is maintained or slightly reduced, the balloons removed from the pipe and then coated in the usual manner with the liquid formulation. After coating, before or during or after the evaporation of the solvents the balloons are evacuated so that either they achieve the desired small cross-section through contraction of the elastic material or they are folded and the folds rolled around the shaft as is usual, for example, in the case of balloons made of nylon.

Preferred active substances are paclitaxel and other taxans, rapamycin and other TOR-binding substances such as everolimus, zotarolimus, biolimus etc., corticoids and their lipophilic derivatives such as betamethasone diproprionate or dexamethasone-21-palmitate, statins such as atorvastatin, cerivastatin or fluvastatin; anticoagulants and platelet aggregation inhibitors such as heparin and its fragments and derivatives, hirudine, acetylsalicylic acid, ticlopidine, clopidogrel, prasugrel, iloprost or other prostacyclins or prostaglandins such as E1, E2, F2α or warfarin, phenprocoumon, particularly preferable on the one hand are paclitaxel, rapamycin and betamethasone proprionate, and anticoagulants such as heparin and hirudine on the other hand. The active substances or their salts can be used individually or in combination with each other. Suitable doses can be between 100 µg/cm balloon length and 10 mg/cm balloon length, preferred are 300-3000 µg/cm balloon length and particularly preferred 600-3000 µg/cm. If a balloon is coated with more than one active substance the above figures relate to the total of the doses of the individual substances. In addition, on its surface or in a structure of the balloon membrane alone, or in combination with synthetic substance, the balloon can contain biological substances such as, for example, proteins, polysaccharides, pentagalloyl glucose, lipids such as nitrooleic acid, hormones and/or nucleic acids; particularly suitable are gelatines and other, also synthetic gel formers, antibodies, micro-RNA, micro-RNA inhibitors such as inhibitors of miR-20, preferred is gelatine, particularly preferred is nitrooleic acid. In this way the balloon is suitable for administering medicinal products or other substance directly to the vascular wall segment being treated.

Surprising is the high loading capacity in spite of the small available surface area of the balloons in the contracted state. In the case of conventional low-elastic nylon balloons the entire final surface area of the balloon membrane is available for coating, e.g. in a balloon with a diameter of 6 mm and a length of 5 cm a (cylindrical) surface area of 942 $mm^2$. The small cross-section of the nylon balloons for insertion into the arteries is achieved through folding as a result of which the membrane surface area does not change.

However, in the contracted state a Chronoprene™ balloon for a vessel with the same diameter (6 mm) only has an area measuring 235 $mm^2$ (external diameter contracted 1.5 mm) or 314 $mm^2$ (external diameter contracted 2.0 mm) for coating but carries the same medicinal product dose. At the conventional dose this means 3 $\mu g/mm^2$ for a nylon balloon, and 12 or 9 $\mu g/mm^2$ in the case of a Chronoprene balloon when coated or introduced into an artery. Sufficient for the coating of elastic or highly-elastic balloons in the contracted state is a coating of ≥5 $\mu g/mm^2$, preferred is a coating with >10 $\mu g/mm^2$ of the surface.

Because of the easy deformability of the elastic membranes it can be important to keep friction of the coating on valves, introductory sheaths and guide catheter and in the blood vessels to low levels. Reducing friction becomes more important the longer the balloon is. Friction on expandable balloons can lead to displacement of the balloon material in the direction of the longitudinal axis, to undesirable folding and deformations and to losses of medicinal product as well as to uneven transmission of the medicinal product to the vascular wall. To improve lubrication physiologically tolerable, preferably solid lubricants can be used such as magnesium stearate, calcium stearate, zinc stearate, magnesium palmitate, zinc palmitate, magnesium myristate, calcium myristate, magnesium laurate, calcium laurate, magnesium caprinate, calcium caprinate, magnesium caprylate, calcium caprylate, magnesium oleate, calcium oleate, magnesium palmitoleate, or calcium palmitoleate. One or more of the following substances can be added: stearic acid, palmitic acid, lauric acid, caprinic acid, caprylic acid, oleic acid, palmitoleic acid stearyl alcohol, polmityl alcohol, lauryl alcohol, magnesium acetate and/or calcium acetate as well as organic salts of said fatty acids, for example salts with ethanol amine, aminopropandiol, serinol, glucosamine, tris (tris(hydroxyl-methyl)amino methane), methyl glucamine, basic amino acids such as lysine or arginine. Preferred are acidic, neutral or at least weakly alkaline fatty acid salts or mixtures. These substances can be used individually or mixed with each other or in combination with one or more pharmacologically active substances. Coatings which improve the lubrication can be applied to the balloon membrane, but also to the catheter shaft.

Additionally additives and excipients can be added for the chemical or pharmaceutical stabilisation of the coating and also the balloon membrane. Preferred are antioxidants such as ascorbic acid, ascorbyl palmitate, butylated hydroxytoluene, butylated hydroxyanisol, nordihydroguaiaretic acid, proplyl gallate, resveratrol, particularly preferred are nordihydroguaiaretic acid, proplyl gallate, resveratrol. Also suitable are substances which have been tried and tested in the coating of conventional angioplasty balloons, more particularly radiographic contrast agents and urea. Numerous possible additives were described in (EP 2170421, U.S. Pat. No. 8,244,344).

Because of its versatile properties ascorbyl palmitate is also of particular interest.

If the balloons are coated with several components the coating can take place with all the components at the same time or initially with one component or one of the component mixtures and then with more or more further components. Substances which improve the lubrication of the balloon can preferably be applied as an outer covering layer.

Coating can take place with conventional method in the contracted, partially or fully expanded state with liquid preparation through immersion, spraying or the application of a defined volume or also through printing technology or with the aid of solids, for example as powders or micro and/or nanoparticles definable in size.

One possible process for the production of balloon catheters with coated expandable balloons can in general be described as follows:

1. Provision of tubes (=balloons) made of elastic materials such as rubber, latex, polyurethane, isoprene-based polymers or copolymers, silicone, particularly preferably from latex or ChronoPrene®.

2. Pre-stretching of the elastic tubes perpendicularly to the longitudinal axis over their entire length, preferably by 3 or more times the original diameter, for example through inflation, returning to the original state through pressure reduction, i.e. to the original diameter.

3. Provision of coaxial catheter shafts with an inner tube with a wire lumen, a liquid lumen, connection of a liquid-filled syringe and radiographically visible markers on the proximal and distal fastening site or the elastic tube.

4. Placing of the distal section of the catheter shaft in the tube so that distal outlet of the liquid lumen of the catheter shaft comes to lie in the tube and the proximal radiographically visible marker is distal of the proximal tube end, e.g. around 3 mm distal of the proximal tube end. The wire lumen should distally project from the elastic tube by slightly more than one tube length.

5. Fastening of the proximal tube end on the shaft through adhesion and securing by means of a surgical suture.

6. Stretching of the elastic tube in the longitudinal direction to 1.2 to 2.2 times the original length.

7. Fastening of the tube approx. 1 cm proximal of distal tube end containing the wire lumen through adhesion and securing by means of a surgical suture.

8. Visual inspection

9. Checking for tightness through the application of a vacuum and/or placing in a tube and applying a pressure of 2.0266-4.0532 bar (2-4 atms), deflation.

10. Packing and sterilization

The following examples shows the structure of the balloons, the coating with a selected medicinal product, its adhesion on the balloon material, the method of functioning when expanding in blood vessels as well as the release of the active substance on expansion in the tissue and transmission into the vascular wall sufficient for the effect.

EXAMPLE 1

Polyurethane balloons which in the deflated state are 2 mm in diameter and 5 cm in length, mounted on the distal end of catheters, were coated with 40 μl of a solution of paclitaxel in acetone/water 50 mg/ml by means of a Hamilton micro-syringe. On analysis there were 1708 μg of paclitaxel on the balloons. On expansion of the balloons in the dry state to a diameter of 10 mm, 80% of the paclitaxel still remained on the balloon surface. After expansion with approximately 0.5 bar in a porcine iliac artery, 15% of the dose was found in the arterial tissue, 6% remained on the balloon.

EXAMPLE 2

Small balloons with silicone membrane which in the deflated state are 2 mm in diameter and 1 cm in length, mounted on the distal end of catheters were coated with a solution of paclitaxel (50 mg/ml) and nordihydroguaiaretic acid (10 mg/ml) in acetone/ethanol/water. On analysis 637 μg paclitaxel were found on the balloons. On expansion at 2 bar of the balloons in the dry state up to a diameter of 10 mm, 87% of the paclitaxel still remained on the balloon surface.

EXAMPLE 3

Latex balloons which after pre-stretching are 5 cm long, were mounted on catheter shafts with a wire lumen measuring 0.0889 (0.035") in diameter. The balloons were coated with 40 μl of a solution of paclitaxel (50 mg/ml) and nordihydroguaiaretic acid (15 mg/ml) in acetone/ ethanol/ water by way of a Hamilton micro-syringe. 1752±30 μg paclitaxel were found on the balloons. The balloons were inflated with a maximum pressure of 2 bar in porcine peripheral arteries. A short time later 4.4±2.5% of the dose was found in the porcine arterial walls while 9.9±9% of the dose remained on the balloons after removal from the animals.

FIG. 3b of the radiographic images in FIGS. 3a and 3 shows the adaptation of a balloon to the diameter, decreasing to distal, and the side branches of the treated artery. In FIG. 3a the treated area is shown by arrows. The treatment results in smoothing of vascular walls, the application of dissections to the wall and the transmission of a medicinal product into the tissue.

EXAMPLE 4

Chronoprene® balloons with a length of 2.5 cm and an external diameter of 2 mm were pre-stretched to a length of 4.5 cm and mounted on catheter shafts with a wire lumen of 0.0889 cm (0.035") in diameter. The balloons were coated with 50 μl of a paclitaxel solution with 50 mg/ml in 75% acetone/25% methanol. The medicinal product content of the balloon after coating was 2104±248 μg. After passing through a haemostatic valve, a 1 m long guide catheter filled with blood, and being held for 1 minute in moving blood 81±8% of the dose still remained on the balloons; shortly after inflation of the balloons for 1 minute in a porcine peripheral artery at approximately 1 bar, 6% of the dose was found in the tissue. This largely corresponds to the transmission of active substance through non-stretchable balloons on application of high pressures (Scheller et al. 2004).

EXAMPLE 5

Before processing, Chronoprene® balloons, Dunn Industries Inc., USA, 2 mm in diameter, were fully expanded without external limitation in air at approximately 1 bar (diameter over the entire length approximately 10 mm) and then deflated (back to the original diameter of 2 mm). Segments of 10 cm in length were pre-stretched to 20 cm in length, mounted on coaxial shafts with a 0.0889 cm (0.035") wire lumen in accordance with FIG. 1 and tested for tightness. The catheters were sterilised in the conventional manner with ethylene oxide. After introducing into porcine leg arteries the balloons were filled with 4-7 ml of contrast agent. The pressure in the catheter lumen was <0.50665 bar (0.5 atm.). In spite of the small pressure the balloons were evenly expanded, the balloon diameter corresponded with the course of the artery, proximally approximately 7 mm, distally 4 mm, with identifiable filling of the exits of side branches similar to FIG. 3b.

EXAMPLE 6

Chronoprene™ balloons, Dunn Industries Inc., USA, 1.5 mm external diameter, internal diameter 1.01 mm, pre-stretched 18 mm to 36 mm, mounted on Rx shafts 0.0356 cm (0.014"), coated in the non-inflated state with 25 mg/ml paclitaxel+1.25 mg/ml nitrooleic acid+5 mg /ml NDGA in acetone/MeO/H$_2$O, application volume=54 μl; paclitaxel content of the balloons: 1140±69 μg (=dose); after passing through a haemostatic valve, a guide catheter 1 m long filled with blood, and being held for 1 minute in moving blood 87±11% of the dose remained on the balloons.

The test shows good adhesion of the active substance on the balloon during simulation of the route to the artery to be treated.

EXAMPLE 7

Chronoprene™ balloons, Dunn Industries Inc., USA, 1.5 mm external diameter, internal diameter 1.1 mm, Q-Medica shaft biluminal 0.046 cm (0.018"), pre-stretched 20 mm to 40 mm, in the non-inflated state coated with 25 mg/ml paclitaxel+1.25 mg/ml nitrooleic in acetone/MeOH/H$_2$O application volume=54 μl; paclitaxel content of the balloons: 1236±27 μg (=dose); the balloons were introduced into porcine internal or external iliac arteries, expanded there for 1 minute, deflated and retracted. 10 minutes after the treatment the anaesthetised animals were killed and the paclitaxel content on the used balloons as well as the treated arterial walls was determined by means of HPLC/UV detection. 5.8±3.3% of the dose remained on the balloons, 14.0±5.0% of the dose was found in the vascular walls (n=6 in each case).

The test shows the largely complete release of the medicinal product from the balloon and the transmission of an in accordance with current knowledge effective portion of the dose to the vascular well.

LIST OF REFERENCE NUMBERS

1 Balloon membrane
2 Distal fastening site of the balloon
3 Proximal fastening site of the balloon
4 Catheter shaft/inner tube with wire lumen
5 Catheter shaft/external tube with liquid lumen
7 Distal end of the catheter
8 Seal
9 Stop
10 Radiographic marker
11 Radiographic marker
12 Tube section
4' Catheter shaft, wire lumen
4" End section
5' Catheter shaft including liquid lumen

The invention claimed is:

1. A balloon catheter for treating a segment of a vessel, said balloon catheter comprising:
(a) a balloon, in the shape of a uniform tube, having a balloon membrane comprising at least one stretchable elastomer, wherein said balloon has a longitudinal axis and a diameter perpendicular to said longitudinal axis, and, when dilating said balloon into a dilated state said diameter can be increased by at least a factor of 2.5 compared to the diameter of said balloon when in a non-dilated state, and wherein said balloon in the non-dilated state has a length which is ≥10 cm or which is >10 times a diameter of a segment of the vessel to be treated, and
(b) a catheter shaft, wherein said catheter shaft forms a wire lumen designed for guiding a guide wire, and a fluid lumen, via which a fluid can be supplied to the balloon, wherein:
said balloon catheter is capable of treating elongated abnormalities in vessels with different lumen diameters and branches though mechanical smoothing;
said catheter shaft comprises a first catheter shaft element and a second catheter shaft element;
said balloon is attached to said first catheter shaft element at a first, proximal fastening site;
said balloon is attached to said second catheter shaft element at a second, distal fastening site, wherein the balloon also surrounds a section of the catheter shaft which extends between the first and second fastening sites; and
upon longitudinal dilation of said balloon, the length of the catheter shaft that is surrounded by said balloon is greater than the length of the catheter shaft when said balloon is in the non-dilated state;
wherein, at an internal pressure of between 0.10133 bar (0.1 atm.) and less than 2.2066 bar (2 atm.) above an external pressure in an area surrounding the balloon, the diameter of the balloon increases at least 2.5 times.

2. The balloon catheter according to claim 1, wherein the at least one stretchable elastomer is selected from the group consisting of rubber, latex, polyurethane, isoprene-based polymers and copolymers, silicone, and copolymers of polystyrene and hydrated isoprene.

3. The balloon catheter according to claim 1, wherein the length of the balloon in the non-dilated state is ≥15 cm.

4. The balloon catheter according to claim 3, wherein the length of the balloon in the non-dilated state is ≥20 cm.

5. The balloon catheter according to claim 1, wherein the balloon and/or the catheter shaft has a physiologically tolerable lubricant on an outer surface thereof.

6. The balloon catheter according to claim 1, wherein the balloon is coated with at least one medicinal product.

7. The balloon catheter according to claim 6, wherein the balloon is coated with at least one medicinal product at a dose of between 100 μg/cm balloon length and 10 mg/cm balloon length.

8. The balloon catheter according to claim 7, wherein the balloon is coated with at least one medicinal product at a dose of between 300 µg/cm balloon length and 3000 µg/cm balloon length.

9. The balloon catheter according to claim 8, wherein the balloon is coated with at least one medicinal product at a dose of between 600 µg/cm balloon length and 3000 µg/cm balloon length.

10. The balloon catheter according to claim 6, wherein the at least one medicinal product is selected from the group consisting of paclitaxel, other taxanes, rapamycin, everolimus, zotarolimus, biolimus, betamethasone diproprionate, dexamethasone-21-palmitate, atorvastatin, cerivastatin, fluvastatin, heparin, hirudin, acetyl salicylic acid, ticlopidin, clopidogrel, prasugrel, iloprost, prostaglandin E1, E2, F2α, warfarin, and phenprocoumone.

11. The balloon catheter according to claim 1, wherein the balloon is coated with at least one antioxidant.

12. The balloon catheter according to claim 11, wherein the balloon is coated with at least one antioxidant selected from the group consisting of ascorbic acid, ascorbyl palmitate, butylated hydroxytoluene, butylated hydroxyanisol, nordihydroguaiaretic acid, propyl gallate, resveratrol, and nitro oleic acid.

13. The balloon catheter according to claim 1, wherein the at least one stretchable elastomer is latex.

14. A method of pre-treating a balloon for a balloon catheter according to claim 1, comprising dilating the balloon before use at least once over a full length perpendicularly to a longitudinal axis by a factor of at least 1.1 in relation to a diameter of the balloon before expansion, without restricting the dilation of the balloon perpendicularly to the longitudinal axis.

15. A method of assembling a balloon on a catheter shaft for a balloon catheter according to claim 1, comprising dilating the balloon along a longitudinal axis by 20% to 120% compared with a state at rest and mounting the balloon on the catheter shaft while maintaining this dilation.

16. A balloon catheter for treating a segment of a vessel, said balloon catheter comprising:
   (a) a balloon, in the shape of a uniform tube, having a balloon membrane comprising at least one stretchable elastomer, wherein said balloon has a longitudinal axis and a diameter perpendicular to said longitudinal axis, and, when dilating said balloon into a dilated state said diameter can be increased by at least a factor of 2.5 compared to the diameter of said balloon when in a non-dilated state, and wherein said balloon in the non-dilated state has a length which is ≥10 cm or which is >10 times a diameter of a segment of the vessel to be treated, and
   (b) a catheter shaft, wherein said catheter shaft forms a wire lumen designed for guiding a guide wire, and a fluid lumen, via which a fluid can be supplied to the balloon, wherein:
said balloon catheter is capable of treating elongated abnormalities in vessels with different lumen diameters and branches though mechanical smoothing;
said catheter shaft comprises a first catheter shaft element and a second catheter shaft element;
said balloon is attached to said first catheter shaft element at a first, proximal fastening site;
said balloon is attached to said second catheter shaft element at a second, distal fastening site, wherein the balloon also surrounds a section of the catheter shaft which extends between the first and second fastening sites; and
upon longitudinal dilation of said balloon, the length of the catheter shaft that is surrounded by said balloon is greater than the length of the catheter shaft when said balloon is in the non-dilated state;
wherein, at an internal pressure of <2.0266 bar (2 atm.) above an external pressure in an area surrounding the balloon, the diameter of the balloon increases at least 2.5 times, the balloon is stretched by 20% to 120% in a longitudinal direction compared to when at rest, and after fastening to the first and second catheter element remains under tension in the longitudinal direction, wherein the elastic balloon material has been pre-stretched perpendicularly to the longitudinal axis by at least a factor of 3 and is tension-free in this direction.

* * * * *